US010143603B2

(12) United States Patent
Nomoto et al.

(10) Patent No.: US 10,143,603 B2
(45) Date of Patent: Dec. 4, 2018

(54) INDIVIDUAL PACKAGE FOR ABSORBENT ARTICLE

(71) Applicant: UNICHARM CORPORATION, Ehime (JP)

(72) Inventors: Takashi Nomoto, Kagawa (JP); Hikari Kawakami, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/756,381

(22) PCT Filed: Jun. 23, 2016

(86) PCT No.: PCT/JP2016/068721
§ 371 (c)(1),
(2) Date: Feb. 28, 2018

(87) PCT Pub. No.: WO2017/043152
PCT Pub. Date: Mar. 16, 2017

(65) Prior Publication Data
US 2018/0243146 A1 Aug. 30, 2018

(30) Foreign Application Priority Data

Sep. 7, 2015 (JP) .................................. 2015-175597

(51) Int. Cl.
*A61F 13/15* (2006.01)
*A61F 13/551* (2006.01)

(52) U.S. Cl.
CPC ................................ *A61F 13/5514* (2013.01)

(58) Field of Classification Search
CPC .......................... A61F 13/5513; A61F 13/5514
(Continued)

(56) References Cited

U.S. PATENT DOCUMENTS 5,462,166 A * 10/1995 Minton ............... A61F 13/5514
206/440
5,484,636 A * 1/1996 Berg, Jr. .............. A61F 13/5514
206/440
(Continued)

FOREIGN PATENT DOCUMENTS

EP 2659866 A1 11/2013
EP 2689757 A1 1/2014
(Continued)

OTHER PUBLICATIONS

International Seach Report for PCT/JP2016/068721, dated Sep. 13, 2016, 4 pages.

*Primary Examiner* — Luan K Bui
(74) *Attorney, Agent, or Firm* — Hauptman Ham, LLP

(57) ABSTRACT

An individual package for an absorbent article is provided with the absorbent article and a wrapping body containing the absorbent article. The absorbent article has a main body extending in a longitudinal direction and a pair of flaps extending from the main body in opposite directions along the longitudinal direction. Each of the main body and the pair of flaps has a fixing section and the main body and the pair of flaps are fixed to the same face of the wrapping body with the fixing sections interposed therebetween. The wrapping body is provided with a pair of bonding regions bonding the wrapping body, the bonding regions being located outward in the widthwise direction and each having a bonding section and a non-bonding section. The fixing sections of the pair of flaps and the non-bonding sections overlap in the widthwise direction.

7 Claims, 11 Drawing Sheets

(58) Field of Classification Search
USPC ....... 206/440, 441, 494; 604/385.01–385.05, 604/385.14, 385.16
See application file for complete search history.

(56) References Cited

U.S. PATENT DOCUMENTS

| | | | | |
|---|---|---|---|---|
| 7,708,727 | B2* | 5/2010 | Woltman | A61F 13/5514 206/440 |
| 2008/0276570 | A1* | 11/2008 | Kuroda | A61F 13/5514 604/385.02 |
| 2012/0316533 | A1* | 12/2012 | Norimoto | A61F 13/47245 604/385.02 |
| 2013/0317470 | A1* | 11/2013 | Kato | A61F 13/15747 604/385.02 |
| 2014/0012219 | A1* | 1/2014 | Hashino | A61F 13/5514 604/385.02 |

FOREIGN PATENT DOCUMENTS

| | | |
|---|---|---|
| JP | 2006-340982 A | 12/2006 |
| JP | 2012-135449 A | 7/2012 |
| JP | 2012-196338 A | 10/2012 |
| JP | 2012-205709 A | 10/2012 |
| JP | 2013-208325 A | 10/2013 |
| WO | 2007/041212 A1 | 4/2007 |
| WO | 2013/031647 A1 | 3/2013 |

* cited by examiner

INDIVIDUAL PACKAGE FOR ABSORBENT ARTICLE

RELATED APPLICATIONS

The present application is a National Phase of International Application Number PCT/JP2016/068721 filed Jun. 23, 2016, and claims priority to Japanese Application Number 2015-175597 filed Sep. 7, 2015.

TECHNICAL FIELD

The present disclosure relates to an individual packaging body of an absorbent article.

BACKGROUND ART

An individual packaging body of an absorbent article is known, in which an absorbent body such as a sanitary napkin, a panty liner, a disposable diaper, etc., is packaged one by one by a packaging sheet, whereby is individually packaged. By individually packaging an absorbent article, an absorbent article can be carried one by one easily and sanitarily.

For example, in Patent Literature 1, a packaging body of an absorbent article is described, comprising the absorbent article which includes an absorbent main body that has a liquid permeable top sheet, a liquid impermeable back sheet and an absorbent body disposed between the top sheet and the back sheet, and a packaging sheet which individually packages the absorbent article, wherein the absorbent article is individually packaged by folding the packaging sheet and the absorbent article in a state in which the absorbent article is disposed over the packaging sheet, a fold is formed in the packaging sheet and the absorbent article, along a longitudinal direction of the absorbent article, in a state in which the individually packaged absorbent article is opened, and the fold includes a first fold at which the absorbent article and the packaging sheet are folded back toward the top sheet side, and a second fold adjacent to the first fold, at which the absorbent article and the packaging sheet are folded back toward the back sheet side.

CITATION LIST

Patent Literature

PTL 1: Japanese Unexamined Patent Publication No. 2012-135449

SUMMARY OF INVENTION

Technical Problem

Patent Literature 1 does not refer to the joining of the packaging sheet, and accordingly, there is room for improvement from the viewpoint of suppressing the intrusion of foreign matter, such as dust, etc.

Accordingly, the object of the present disclosure is to provide an individual packaging body of an absorbent article which is difficult for foreign matter to enter inside the individual packaging body, and has an excellent unsealing property.

Solution to Problem

The present inventors has found out that an individual packaging body of an absorbent article, comprising the absorbent article which includes a longitudinal direction and a width direction, and a packaging body which envelops the absorbent article, wherein the absorbent article includes a main body portion which extends in the longitudinal direction, and a pair of flap portions which extend from the main body portion toward both side portions in the longitudinal direction, the main body portion and the pair of flap portions respectively have a fixed portion, and the main body portion and the pair of flap portions are fixed to a same surface of the packaging body through the respective fixed portions, the packaging body includes, on an outer side in the width direction of the main body portion, a pair of joining regions which join the packaging body and each of which including a joining portion and a non-joining portion, and the fixed portion in each of the pair of flap portions and the non-joining portion are overlapped with each other in the width direction, is the solution to the problem.

Effect of Invention

The individual packaging body of an absorbent article according to the present disclosure makes it difficult for foreign matter to enter inside the individual packaging body, and has an excellent unsealing property.

DESCRIPTION OF EMBODIMENTS

Definitions

Figure 1:
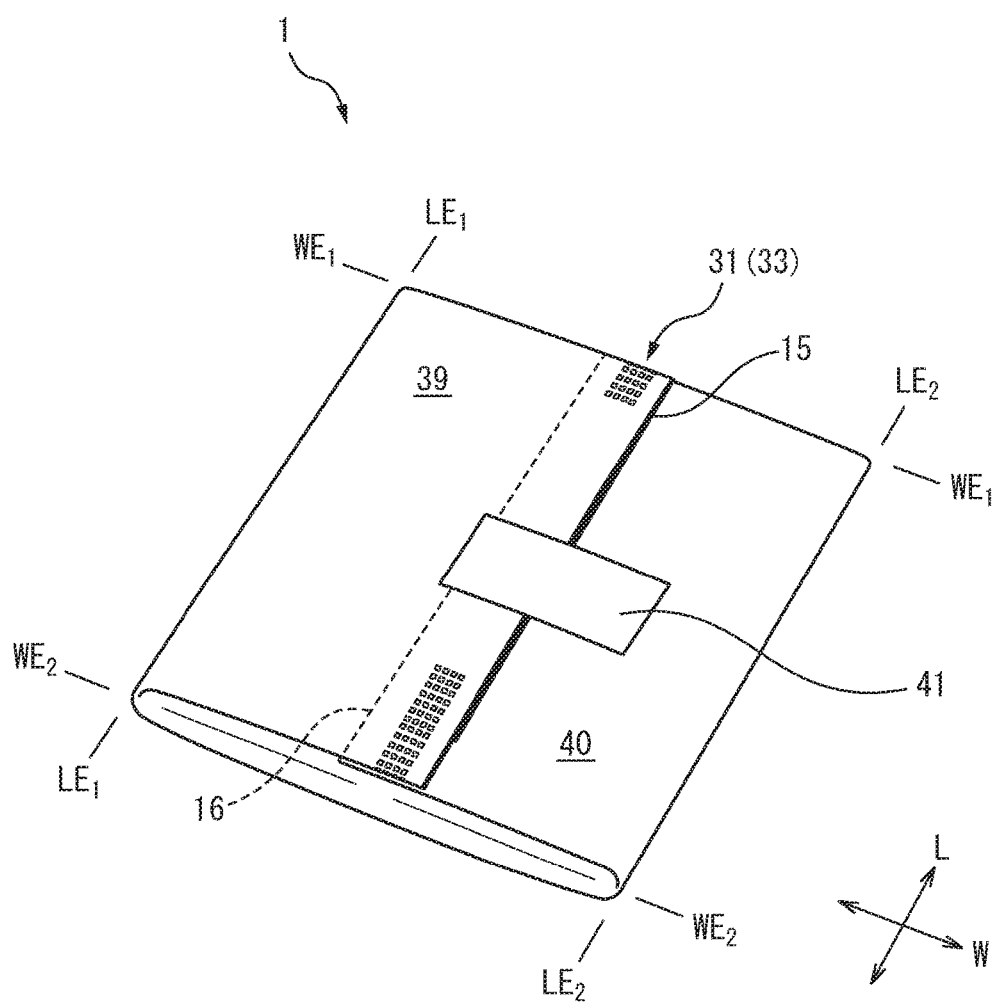
FIG. 1 is a perspective view of an individual packaging body 1 according to a first embodiment.

"a longitudinal direction" and "a width direction"

In the present description, unless otherwise noted, "the longitudinal direction" and "the width direction" respectively mean the longitudinal direction and the width direction of an absorbent article. For example, in the present description, there may be a case in which the longitudinal direction and the width direction are mentioned in relation to a packaging body, an individual packaging body, etc., however, unless otherwise noted, they are based on the longitudinal direction and the width direction of an absorbent article.

"a joining portion which is disposed on a width direction first expansion line side" and "a joining portion which is disposed on a width direction second expansion line side"

In the present description, "the joining portion which is disposed on a width direction first expansion line side" means a joining portion which is disposed closer to the width direction first expansion line than to a center line of the width direction first expansion line and the width direction second expansion line. In the same manner, "the joining portion which is disposed on a width direction second expansion line side" means a joining portion which is disposed closer to the width direction second expansion line than to the above mentioned center line.

The absorbent article of the present disclosure relates to the following aspects.

[Aspect 1]

An individual packaging body of an absorbent article, comprising the absorbent article which includes a longitudinal direction and a width direction, and a packaging body which envelops the absorbent article, wherein the absorbent article includes a main body portion which extends in the longitudinal direction, and a pair of flap portions which extend from the main body portion toward both side portions in the longitudinal direction, the main body portion and the pair of flap portions respectively have a fixed portion, and the main body portion and the pair of flap portions are fixed to a same surface of the packaging body through the respective fixed portions, the packaging body includes, on an outer side in the width direction of the main body portion, a pair of joining regions which join the packaging body and each of which including a joining portion and a non-joining portion, and the fixed portion in each of the pair of flap portions and the non-joining portion are overlapped with each other in the width direction.

In the individual packaging body as described in aspect 1, since the packaging body includes the pair of joining regions each of which including the joining portion and the non-joining portion, the individual packaging body makes it difficult for foreign matter, such as dust, etc., to enter inside the individual packaging body, from the both side portions of the packaging body (from the one side portion and the other side portion). Further, in the individual packaging body as described in aspect 1, since the fixed portion of the pair of flap portions and the non-joining portion of the packaging body overlap with each other in the width direction of the absorbent article, in the individual packaging body, when taking off the absorbent article from the packaging body by grasping the longitudinal direction end portion of the absorbent article and the corresponding portion of the above mentioned longitudinal direction end portion of the packaging body, it is difficult for the fixed portion of the pair of flap portions to be attached to the main body portion, etc., whereby the individual packaging body has an excellent unsealing property. Accordingly, the individual packaging body as described in aspect 1 makes it difficult for foreign matter to enter inside the individual packaging body from the both side portions of the packaging body, and has an excellent unsealing property.

Further, in the conventional individual packaging body of an absorbent article, the one is known in which a pair of flap portions are folded over the main body portion with a liquid permeable sheet placed on the inner side, two fixed portions of the pair of flap portions are adhered with a release sheet, and the absorbent article is packaged by a packaging sheet. The individual packaging body as described in aspect 1 has an effect that, by grasping the longitudinal direction end portion of the absorbent article and the corresponding portion of the above mentioned longitudinal direction end portion of the packaging body, without peeling off the release sheet which is adhered to the fixed portions of the pair of flap portions, the absorbent article can be taken off from the packaging body more easily compared to the conventional individual packaging body.

[Aspect 2]

The individual packaging body according to aspect 1, wherein the packaging body includes at least a width direction first expansion line and a width direction second expansion line each of which extending along the width direction for expanding the individual packaging body, the packaging body includes a first expansion portion, a base body portion, and a second expansion portion which are partitioned by the width direction first expansion line and the width direction second expansion line, and the same surface is an inner surface of the base body portion.

In the individual packaging body as described in aspect 2, the packaging body includes the first expansion portion, the base body portion, and the second expansion portion, and the main body portion and the pair of flap portions are respectively fixed to the inner surface of the base body portion of the packaging body through the fixed portions. Accordingly, when taking off the absorbent article from the packaging body by grasping the longitudinal direction end portion of the absorbent article and the corresponding portion of the above mentioned longitudinal direction end portion of the packaging body, it is even easier for the fixed portions of the pair of flap portions to be attached to the main body portion, etc. However, by satisfying the requirements of the present disclosure, when taking off the absorbent article from the packaging body by grasping the longitudinal direction end portion of the absorbent article and the corresponding portion of the above mentioned longitudinal direction end portion of the packaging body, the unsealing property of the individual packaging body can be retained.

[Aspect 3]

The individual packaging body according to aspect 2, wherein each of the pair of joining regions includes the joining portion which is disposed on a width direction first expansion line side of the individual packaging body, the joining portion which is disposed on a width direction second expansion line side of the individual packaging body, and the non-joining portion which is disposed between the joining portions.

In the individual packaging body as described in aspect 3, each of the pair of joining regions includes the joining portion which is disposed on the width direction first expansion line side, the joining portion which is disposed on the width direction second expansion line side, and the non-joining portion which is disposed therebetween. Accordingly, the above mentioned individual packaging body makes it difficult for foreign matter to enter inside the individual packaging body from the both side portions of the packaging body. Further, in an embodiment in which the above mentioned individual packaging body is further folded along a longitudinal direction folding axis, at each of the both side portions of the individual packaging body in the longitudinal direction of the absorbent article (which are the one side portion and the other side portion), it is difficult for the edges to be shifted, whereby the individual packaging body is excellent in aesthetic appearance.

[Aspect 4]

The individual packaging body according to aspect 3, wherein the second expansion portion is disposed, in a range which overlaps with the non-joining portion and the joining portion that is disposed on the width direction second expansion line side in a thickness direction of the individual packaging body.

In the individual packaging body as described in aspect 4, the second expansion portion is disposed, in a range which overlaps with the non-joining portion and the joining portion that is disposed on the width direction second expansion line side in the thickness direction of the individual packaging body, that is, the second expansion portion is disposed, in a range which does not overlap with the joining portion that is disposed on the width direction first expansion line side in the thickness direction of the individual packaging body. Accordingly, in the above mentioned individual packaging body, since the end portion of the second expansion portion on the opposite side of the base body portion is present in the range which overlaps with the non-joining portion in the thickness direction of the individual packaging body, when the first expansion portion is expanded, and then the longitudinal direction end portion of the absorbent article and the corresponding portion of the above mentioned longitudinal direction end portion of the packaging body are grasped, it is easier for the pair of flaps and the second expansion portion (especially, the end portion of the second expansion portion on the opposite side of the base body portion) to be separated from each other, and for a space to be formed therebetween. As a result, in the above mentioned individual packaging body, when taking off the absorbent article from the packaging body by grasping the longitudinal direction end portion of the absorbent article and the corresponding portion of the above mentioned longitudinal direction end portion of the packaging body, it is difficult for the pair of flap portions to be attached to the main body portion, etc., and the individual packaging body is excellent in the unsealing property.

[Aspect 5]

The individual packaging body according to aspect 4, wherein a length in the longitudinal direction of the range in which the second expansion portion and the non-joining portion overlap with each other in the thickness direction of the individual packaging body, is or longer than 50% of a length in the longitudinal direction of the second expansion portion.

In the individual packaging body as described in aspect 5, the length in the longitudinal direction of the range in which the second expansion portion and the non-joining portion overlap with each other in the thickness direction of the individual packaging body, is or longer than 50% of the length in the longitudinal direction of the second expansion portion. Accordingly, when the first expansion portion is expanded, and the longitudinal direction end portion of the absorbent article and the corresponding portion of the above mentioned longitudinal direction end portion of the packaging body are grasped, it is easier for the pair of flaps and the second expansion portion (especially, the end portion of the second expansion portion on the opposite side of the base body portion) to be separated from each other, and for a space to be formed therebetween, compared to a case in which the requirements of aspect 5 is not satisfied. As a result, in the above mentioned individual packaging body, when taking off the absorbent article from the packaging body by grasping the longitudinal direction end portion of the absorbent article and the corresponding portion of the above mentioned longitudinal direction end portion of the packaging body, it is difficult for the pair of flap portions to be attached to the main body portion, etc., and the individual packaging body is excellent in the unsealing property.

[Aspect 6]

The individual packaging body according to any one of aspects 2 to 5, wherein at least one end portion in the width direction of an expansion end of the first expansion portion is included in the joining portion.

In the individual packaging body as described in aspect 6, the one end portion in the width direction of the absorbent article of the expansion end of the first expansion portion in the individual packaging body is included in the joining portion. Accordingly, it is difficult for the expansion end of the first expansion portion in the individual packaging body to be unsealed by an unintended impact, etc., in a bag, etc.

[Aspect 7]

The individual packaging body according to any one of aspects 2 to 6, wherein the individual packaging body is expandable in the width direction, along two longitudinal direction expansion lines which are disposed on an inner side than the pair of joining regions and extend in the longitudinal direction.

In the individual packaging body as described in aspect 7, the packaging body is expandable in the width direction of the absorbent article, along the two longitudinal direction expansion lines which are parallel to the longitudinal direction of the absorbent article, that is, the individual packaging body is folded along the longitudinal direction expansion lines. Accordingly, since the longitudinal direction expansion lines which are folded suppress the intrusion of foreign matter, such as dust, etc., the above mentioned individual packaging body has an effect of making it difficult for foreign matter to enter inside the individual packaging body from the both side portions of the packaging body.

[Aspect 8]

The individual packaging body according to aspect 7, wherein a distance between the two longitudinal direction expansion lines is or shorter than ½ of a length in the width direction of the packaging body.

In the individual packaging body as described in aspect 8, the distance between the two longitudinal direction expansion lines is or shorter than ½ of the length in the width direction of the absorbent article, of the packaging body. Accordingly, in a state in which the individual packaging body is expandable along the two longitudinal direction expansion lines, that is, a state in which the individual packaging body is folded along the two longitudinal direction expansion lines (the non-expansion state), in between the one region between the one side portion and the one longitudinal direction expansion line in the packaging body and the other region between the other side portion and the other longitudinal direction expansion line in the packaging body, the one region and the other region are to be in a relationship in which the other region is disposed over the one region, or the one region is disposed over the other region. As a result, in the state in which the individual packaging body is folded along the two longitudinal direction expansion lines (the non-expansion state), one side portion of the other side portion of the packaging body is not exposed, and the individual packaging body makes it difficult for foreign matter, such as dust, etc., to enter therein from the one side portion or the other side portion of the packaging body. Accordingly, the above mentioned individual packaging body has an effect of making it difficult for foreign matter to enter inside the individual packaging body from the one side portion or the other side portion of the packaging body.

[Aspect 9]

The individual packaging body according to aspect 7 or 8, wherein an expansion end of the first expansion portion is exposed by expanding the individual packaging body along the two longitudinal direction expansion lines.

In the individual packaging body as described in aspect 9, the expansion end of the first expansion portion is exposed by expanding the individual packaging body along the two longitudinal direction expansion lines. That is, the above mentioned individual packaging body is folded along the two longitudinal direction expansion lines with the expansion end of the first expansion portion placed on the inner side. Accordingly, it is difficult for foreign matter, such as dust, etc., to enter inside the individual packaging body from the expansion end of the first expansion portion. Accordingly, the above mentioned individual packaging body has an effect of making it difficult for foreign matter to enter inside the individual packaging body from the expansion end.

Hereinbelow, the individual packaging body of the absorbent article according to the present disclosure is explained in detail.

FIGS. 1 to 6 are views to explain the individual packaging body 1 of the absorbent article according to one embodiment (the first embodiment) of the present disclosure. Incidentally, in the present description, there may be a case in which "an individual packaging body of an absorbent article" is simply referred to as "an individual packaging body".

Figure 2:
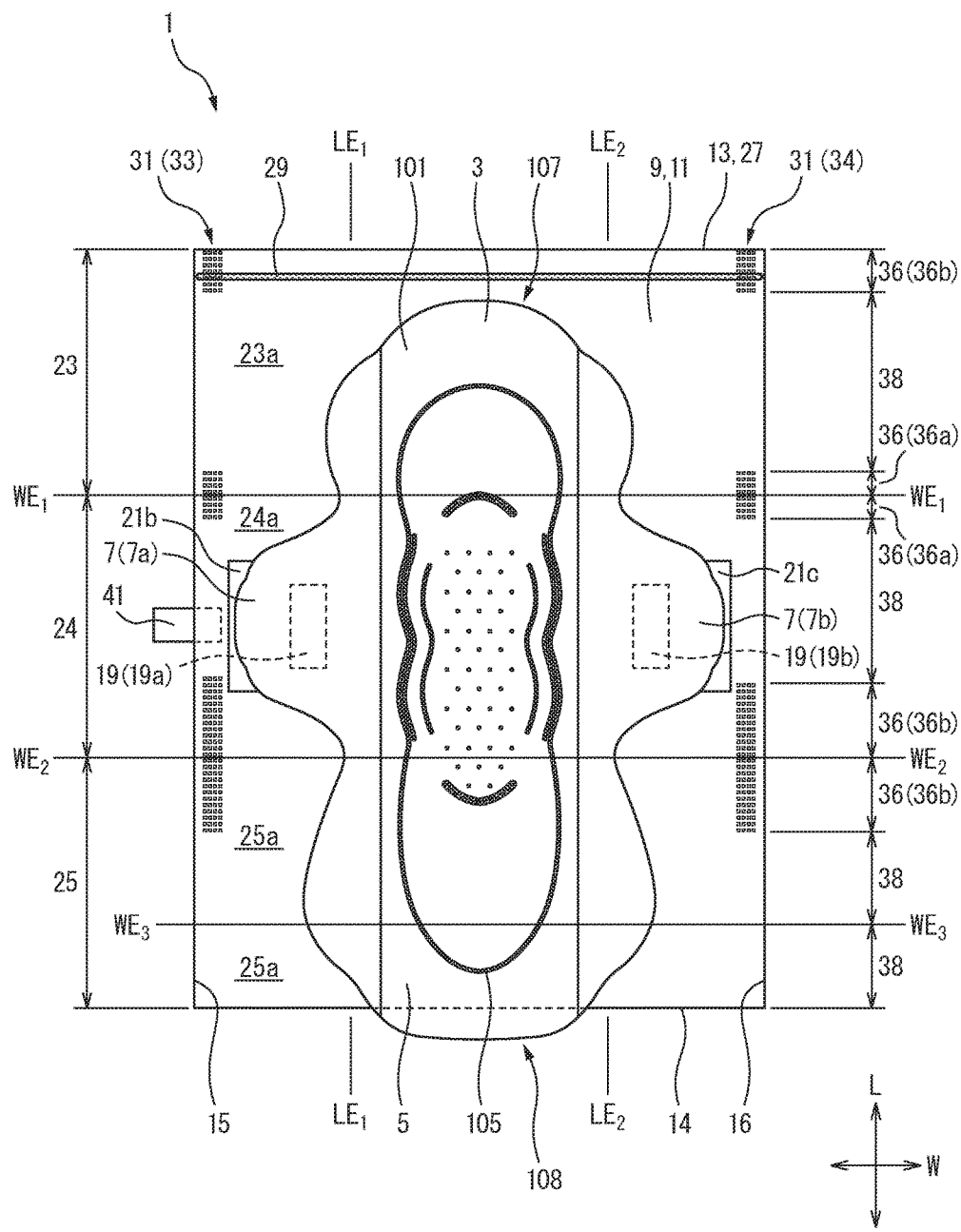
FIG. 2 is an expanded view on a front surface side of the individual packaging body 1 according to the first embodiment.
Figure 3:
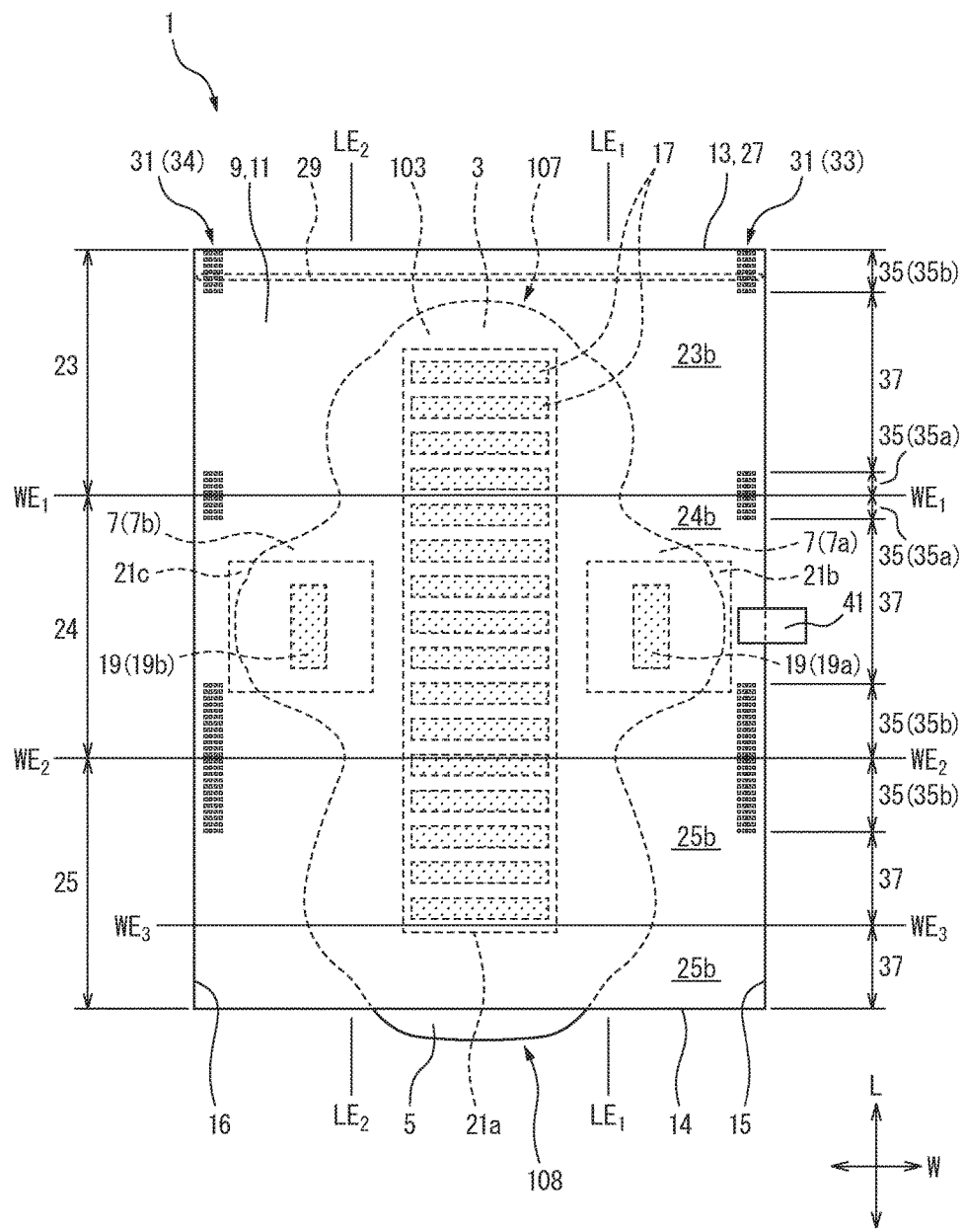
FIG. 3 is an expanded view on a back surface side of the individual packaging body 1 according to the first embodiment.
Figure 4:
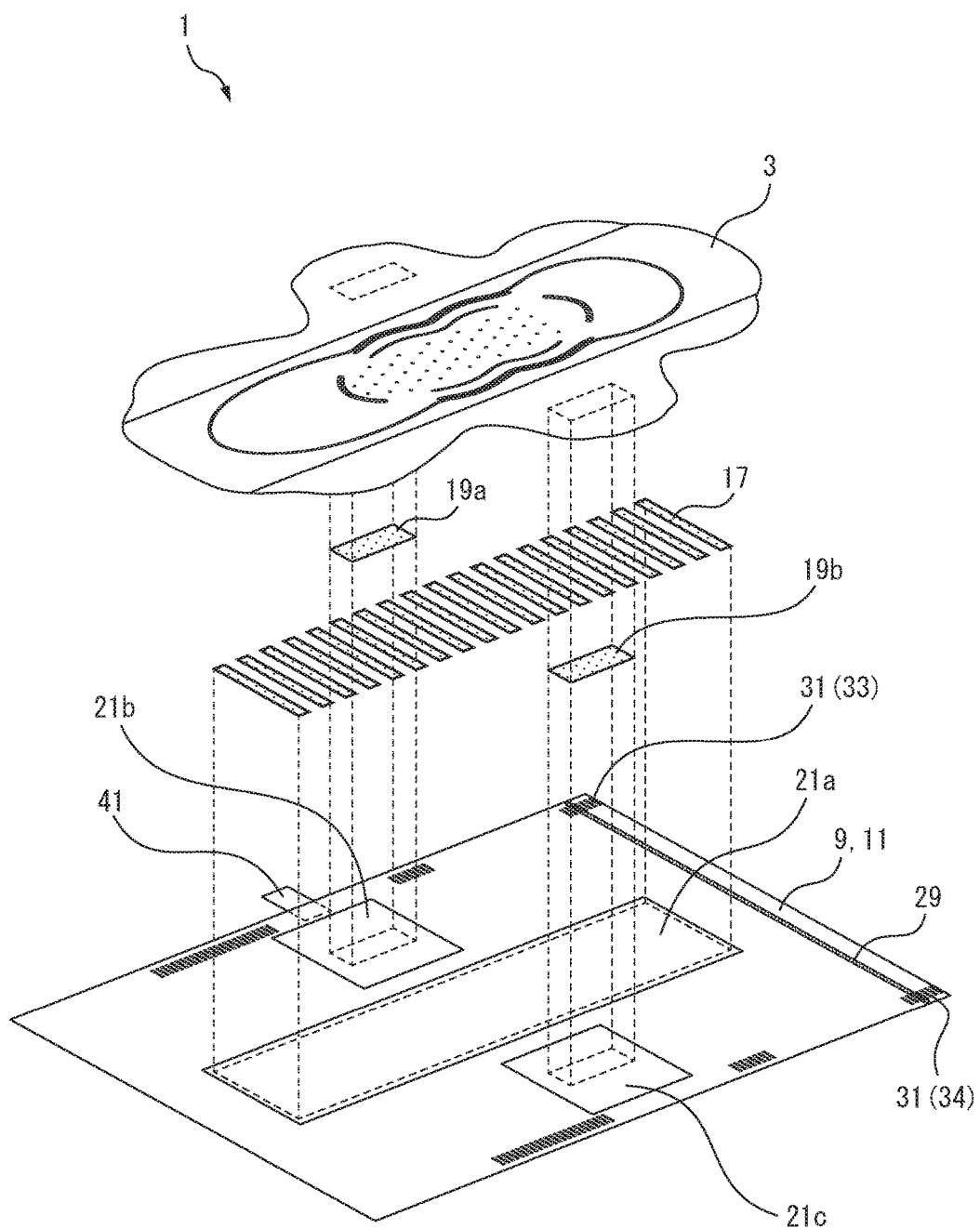
FIG. 4 is an exploded perspective view of the individual packaging body 1 according to the first embodiment.
Figure 5:
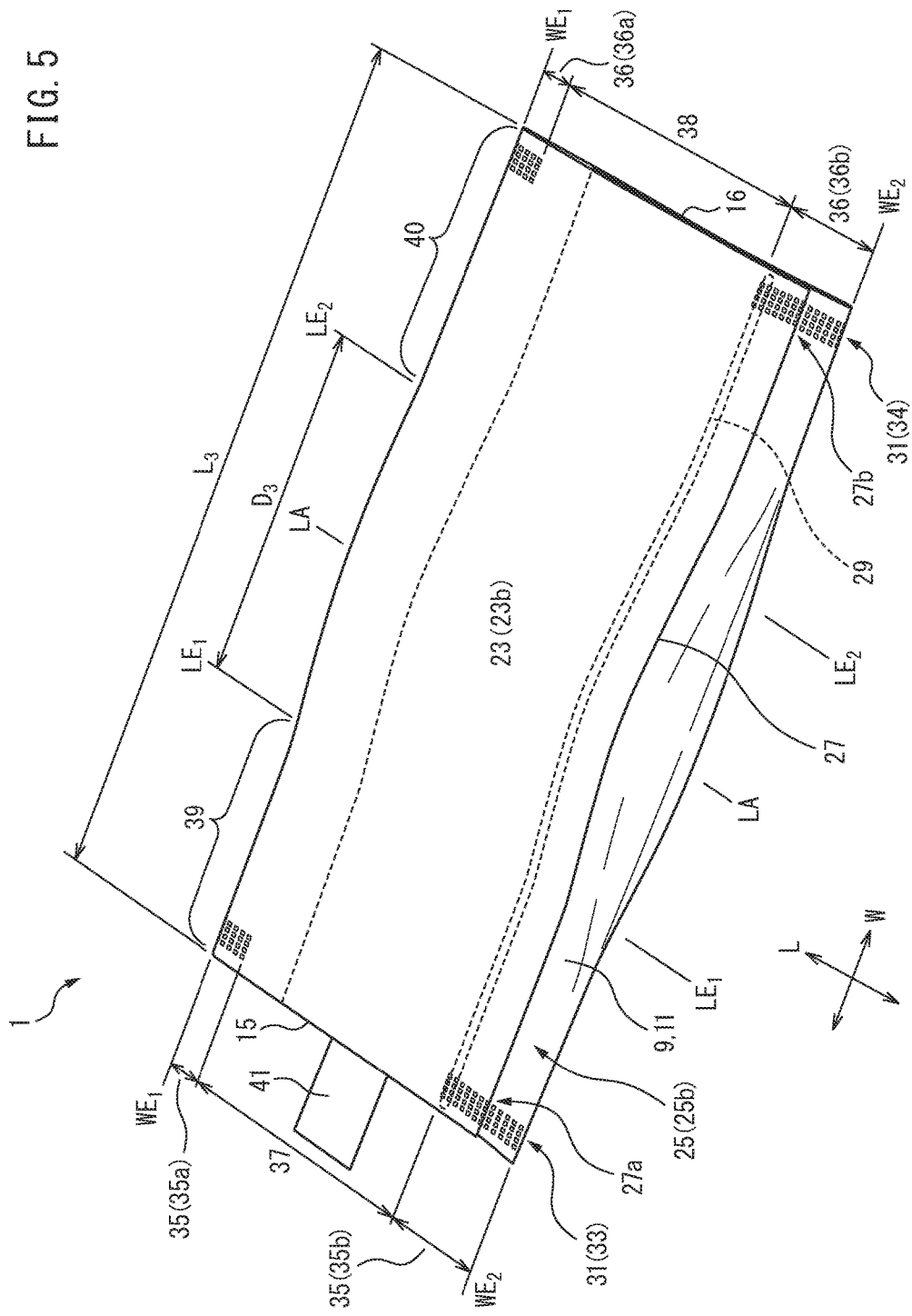
FIG. 5 is a view to explain the individual packaging body 1 according to the first embodiment.
Figure 6:
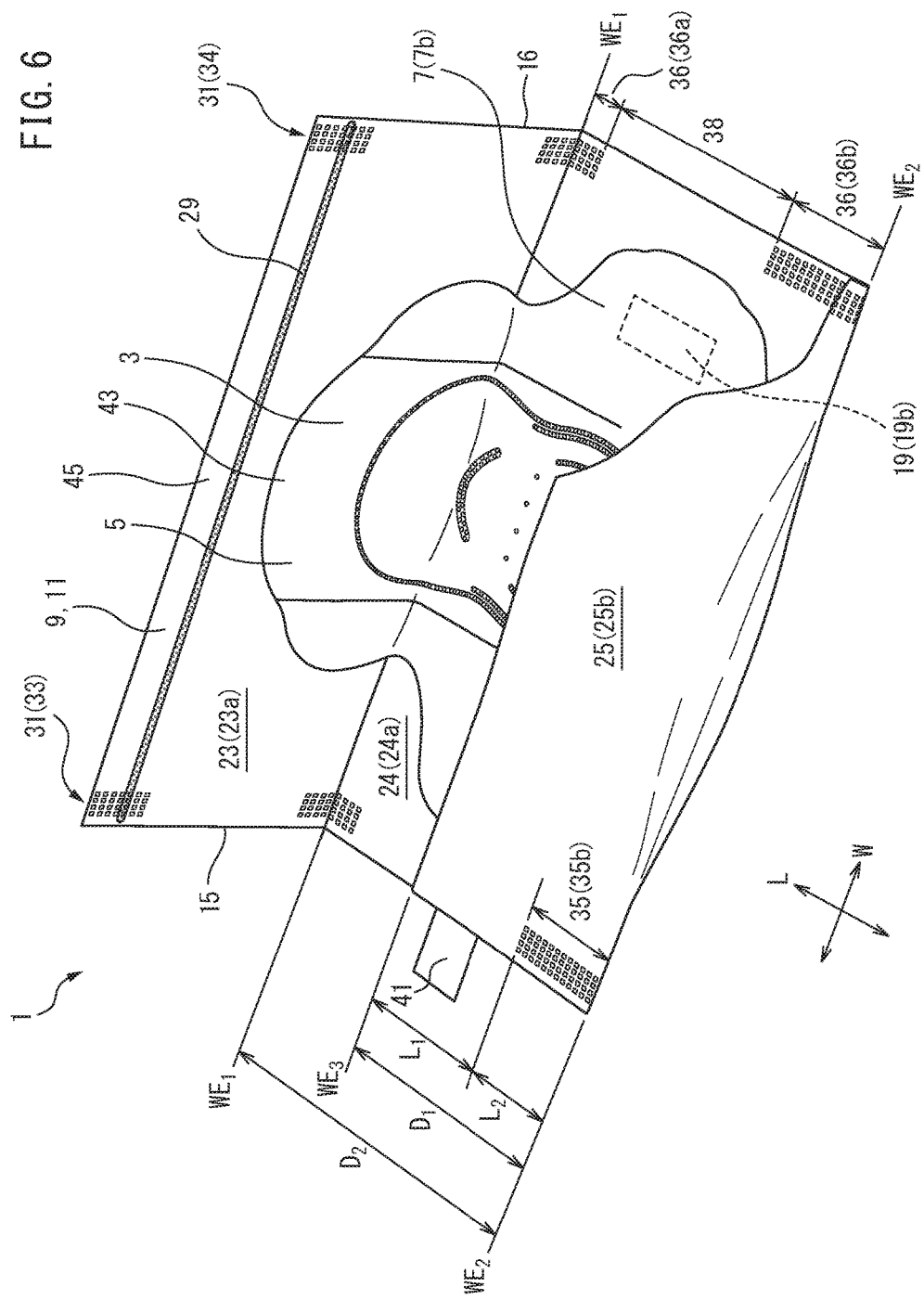
FIG. 6 is another view to explain the individual packaging body 1 according to the first embodiment.

To be more specific, FIG. 1 is a perspective view of the individual packaging body 1 according to a first embodiment, FIG. 2 is an expanded view (a complete expansion view) on a front surface side of the individual packaging body 1 according to the first embodiment, FIG. 3 is an expanded view (a complete expansion view) on a back surface side of the individual packaging body 1 according to the first embodiment, and FIG. 4 is an exploded perspective view of the individual packaging body 1 according to the first embodiment. FIG. 5 is a perspective view of a half expansion state of the individual packaging body 1 according to the first embodiment, and to be more specific, is a perspective view of the individual packaging body 1 being folded at the width direction first expansion line $WE_1$, the width direction second expansion line $WE_2$, and the width direction third expansion line $WE_3$, from the complete expansion state. FIG. 6 is a perspective view in which the first expansion portion 23 is expanded from the individual packaging body 1 in the half expansion state as shown in FIG. 5. Incidentally, in FIG. 6, a portion of the second expansion portion 25 is omitted for explanatory purposes.

Incidentally, in the first embodiment, a state in which the individual packaging body 1 is not expanded (unsealed) is referred to as "a non-expansion state", a state in which the individual packaging body 1 is expanded at the longitudinal direction first expansion line $LE_1$ and the longitudinal direction second expansion line $LE_2$ is referred to as "a half expansion state", and a state in which the individual packaging body 1 is expanded at the width direction first expansion line $WE_1$, the width direction second expansion line $WE_2$, and the width direction third expansion line $WE_3$ from the half expansion state is referred to as "a complete expansion state".

The individual packaging body 1 according to the first embodiment includes, as shown in FIGS. 2 and 3, the absorbent article 3 which includes a longitudinal direction L and a width direction W, and a packaging body 9 which envelops the absorbent article 3. The absorbent article 3 includes a main body portion 5 which extends in the longitudinal direction L, and a pair of flap portions 7 (one flap portion 7a and the other flap portion 7b) which extend from the main body portion 5 toward both side portions in the longitudinal direction L.

The packaging body 9 is formed by a packaging sheet 11.

The absorbent article 3 is a sanitary napkin, and includes a liquid permeable sheet 101, a liquid impermeable sheet 103, and an absorbent body (which is not shown) between the liquid permeable sheet 101 and the liquid impermeable sheet 103. The absorbent article 3 further includes a compressed portion 105 which compresses the liquid permeable sheet 101 and the absorbent body (which is not shown). Further, in the absorbent article 3, the upward direction is the front side 107 and the downward direction is the rear side 108, when facing FIGS. 2 and 3. Incidentally, since the absorbent article 3 has a publicly known configuration, the detailed explanation thereof is omitted.

The packaging sheet 11 has a substantially rectangular shape, and includes the same longitudinal direction L and the same width direction W as the absorbent article 3. The packaging body 9 (the packaging sheet 11) includes, in the longitudinal direction L, the one end portion 13 and the other end portion 14 which respectively correspond to the front side 107 and the rear side 108 in the absorbent article 3. The packaging body 9 (the packaging sheet 11) further includes, in the longitudinal direction L, the one side portion 15 and the other side portion 16 which respectively correspond to one flap portion 7a and the other flap portion 7b of the absorbent article 3.

Incidentally, the wearer takes out the absorbent article 3 from the packaging body 9 by holding the front side 107 of the absorbent article 3, and the corresponding portion of the packaging body 9 (the packaging sheet 11), that is, the one end portion 13 in the longitudinal direction L.

The main body portion 5 of the absorbent article 3 includes a fixed portion 17 which is fixed to the clothing contact surface thereof, and to be more specific, to the clothing contact surface of the liquid impermeable sheet 103. The fixed portion 17 includes a plurality of fixed portion parts each of which extending in the width direction W of the absorbent article 3, and which are disposed at a predetermined interval in the longitudinal direction L of the absorbent article 3.

Further, each of the pair of flap portions 7 of the absorbent article 3 includes a fixed portion 19 which is fixed to the clothing contact surface thereof, and to be more specific, to the clothing contact surface of the liquid impermeable sheet 103. To be more specific, the one flap portion 7a and the other flap portion 7b respectively include the fixed portion 19a and the fixed portion 19b.

The absorbent article 3 is fixed to the packaging body 9 (the packaging sheet 11) through the fixed portion 17 and the fixed portion 19. Incidentally, the packaging body 9 (the packaging sheet 11) includes release papers 21a, 21b, and 21c respectively at portions which are in contact with the fixed portion 17, 19a, and 19b, and the absorbent article 3 is fixed to the packaging body 9 (the packaging sheet 11) in a state capable of being peeled off therefrom. Accordingly, the absorbent article 3 is re-fixed to the clothing of the wearer through the fixed portion 17, 19a, and 19b, when being used.

The absorbent article 3 and the packaging sheet 11 which configures the packaging body 9 are folded, with the absorbent article 3 on the inner side, by three width direction expansion lines which extend in the width direction W, and to be more specific, which are parallel to the width direction W, the three width direction expansion lines being more specifically, the width direction first expansion line $WE_1$, the width direction second expansion line $WE_2$, and the width direction third expansion line $WE_3$, in a state in which the absorbent article 3 is fixed to the packaging sheet 11. The width direction first expansion line $WE_1$, the width direction second expansion line $WE_2$, and the width direction third expansion line $WE_3$ are disposed at a predetermined interval in the longitudinal direction L.

The packaging body 9 (the packaging sheet 11) includes, in the longitudinal direction L, a first expansion portion 23 which is partitioned by the one end portion 13 and the width direction first expansion line $WE_1$, a base body portion 24 which is partitioned by the width direction first expansion line $WE_1$ and the width direction second expansion line $WE_2$, and a second expansion portion 25 which is partitioned by the width direction second expansion line $WE_2$ and the other end portion 14. In other words, the packaging body 9 (the packaging sheet 11) includes the base body portion 24, and the first expansion portion 23 and the second expansion portion 25 which are disposed on both ends in the longitudinal direction L of the base body portion 24. Incidentally, the width direction third expansion line $WE_3$ further partitions the second expansion portion 25 into two regions which are adjacent to each other in the longitudinal direction L.

The first expansion portion 23 includes an inner surface 23a to which the absorbent article 3 is fixed, and an outer surface 23b to which the absorbent article 3 is not fixed, the base body portion 24 includes an inner surface 24a to which the absorbent article 3 is fixed, and an outer surface 24b to which the absorbent article 3 is not fixed, and second expansion portion 25 includes an inner surface 25a to which the absorbent article 3 is fixed, and an outer surface 25b to which the absorbent article 3 is not fixed.

The main body portion 5 and the pair of flap portions 7 (7a, 7b) of the absorbent article 3 are respectively fixed to the same surface of the packaging body 9 (the packaging sheet 11), and to be more specific, to the inner surface 24a of the base body portion 24, through the fixed portion 17, and the fixed portion 19 (19a, 19b).

The main body portion 5 of the absorbent article 3 is fixed to the inner surface of the packaging body 9 through the fixed portion 17, in a state of being sandwiched by the width direction first expansion line $WE_1$ and the width direction second expansion line $WE_2$. To be more specific, the main body portion 5 of the absorbent article 3 is fixed to the inner surface 23a of the first expansion portion 23, to the inner surface 24a of the base body portion 24, and to the inner surface 25a of the second expansion portion 25, through the fixed portion 17, in a state of being sandwiched by the width direction first expansion line $WE_1$ and the width direction second expansion line $WE_2$. In such case, when taking off the absorbent article 3 from the packaging body 9, it is easy for the fixed portion 19 of the pair of flap portions 7 to be attached to the main body portion 5, etc., however, in the individual packaging body 1 according to the first embodiment, the absorbent article 3 can be taken off from the packaging body 9 without the fixed portion 19 of the pair of flap portions 7 being attached to the main body portion 5. The reason thereof is described later.

The absorbent article 3 and the packaging sheet 11 which configures the packaging body 9 are folded, with the absorbent article 3 on the inner side, at the width direction third expansion line $WE_3$, the width direction second expansion line $WE_2$, and the width direction first expansion line $WE_1$, in this order, and the packaging body 9 (the packaging sheet 11) is, as shown in FIGS. 5 and 6, laminated with the base body portion 24, the second expansion portion 25, and the first expansion portion 23, in this order.

The one end portion 13 of the first expansion portion 23 configures an expansion end 27 when the first expansion portion 23 is expanded. The first expansion portion 23 is fixed to the outer surface 25b of the second expansion portion 25 to which the absorbent article 3 is not fixed, through the adhesive portion 29 which is disposed in the vicinity of the expansion end 27 of the inner surface 23a to which the absorbent article 3 is fixed. By the presence of the adhesive portion 29, it is difficult for the foreign matter, such as dust, etc., to enter inside the individual packaging body 1 from the expansion end 27 of the first expansion portion 23.

The packaging body 9 includes pair of joining regions 31 which join the base body portion 24, the second expansion portion 25, and the first expansion portion 23 of the packaging body 9 on the outer side in the width direction W, in a state of being laminated with the base body portion 24, the second expansion portion 25, and the first expansion portion 23, in this order (that is, in a state in which the packaging sheet 11 is folded by the width direction first expansion line $WE_1$, the width direction second expansion line $WE_2$, and the width direction third expansion line $WE_3$, which is the half expansion state). Each of the pair of joining regions 31 is disposed on the outer side in the width direction W of the main body portion 5 of the absorbent article 3, and on the outer side of the pair of flap portions 7 of the absorbent article 3, and extends in the longitudinal direction L. The pair of joining regions 31 are partitioned into one joining region 33 which is on the one side portion 15 side of the packaging body 9, and the other joining region 34 which is on the other side portion 16 side of the packaging body 9.

The one joining region 33 includes, as shown in FIG. 5, a joining portion 35 and a non-joining portion 37. To be more specific, the one joining region 33 is configured by a joining portion 35a which extends from the width direction first expansion line $WE_1$, a joining portion 35b which extends from the width direction second expansion line $WE_2$, and the non-joining portion 37 which is disposed therebetween. Each of the joining portion 35a, the joining portion 35b, and the non-joining portion 37 extends in the longitudinal direction L.

Further, the other joining region 34 includes a joining portion 36, and a non-joining portion 38. To be more specific, the other joining region 34 is configured by a joining portion 36a which extends from the width direction first expansion line $WE_1$, a joining portion 36b which extends from the width direction second expansion line $WE_2$, and the non-joining portion 38 which is disposed therebetween. Each of the joining portion 36a, the joining portion 36b, and the non-joining portion 38 extends in the longitudinal direction L.

As shown in FIG. 5, and as clear from FIG. 6, the second expansion portion 25 is disposed, in the longitudinal direction L, in a range which overlaps with the non-joining portion 37 and the joining portion 35b that extends from the width direction second expansion line $WE_2$, in other words, in a range which does not overlap with the joining portion 35a that extends from the width direction first expansion line $WE_1$, in a state of being folded at the width direction first expansion line $WE_1$, the width direction second expansion line $WE_2$, and the width direction third expansion line $WE_3$ (the half expansion state). In the same manner, the second expansion portion 25 is disposed, in the longitudinal direction L, in a range which overlaps with the non-joining portion 38 and the joining portion 36b that extends from the width direction second expansion line $WE_2$, in other words, in a range which does not overlap with the joining portion 36a that extends from the width direction first expansion line $WE_1$, in a state of being folded at the width direction first expansion line $WE_1$, the width direction second expansion line $WE_2$, and the width direction third expansion line $WE_3$ (the half expansion state).

According to such configuration, when the first expansion portion 23 is expanded from the state of being folded at the width direction first expansion line $WE_1$, the width direction second expansion line $WE_2$, and the width direction third expansion line $WE_3$ (the half expansion state), and then the longitudinal direction end portion 43 of the absorbent article 3 and the corresponding portion 45 of the packaging body 9 which corresponds to the longitudinal direction end portion 43 are grasped, it is easier for the pair of flaps 7 and the second expansion portion 25 (especially, the end portion of the second expansion portion 25 on the opposite side of the base body portion 24) to be separated from each other, and for a space to be formed therebetween.

As a result, when taking off the absorbent article 3 from the packaging body 9 by grasping the longitudinal direction end portion 43 of the absorbent article 3 and the corresponding portion 45 of the packaging body 9, it is difficult for the absorbent article 3 to come in contact with the second expansion portion 25, and it is difficult for the fixed portion 19 of the pair of flap portions 7 to be attached to the main body portion 5, etc. The reason thereof is described later in relation to FIGS. 7 and 8.

As shown in FIG. 5, the both edges in the width direction W of the expansion end 27 of the first expansion portion 23, that is, one edge 27a and the other edge 27b, are respectively included in the joining portion 35b and the joining portion 36b. Accordingly, it is difficult for the first expansion portion 23 of the individual packaging body 1, especially, the expansion end 27, to be unsealed by an unintended impact, etc., in a bag, etc.

Each of the joining portion 35 and the joining portion 36 is formed by intermittently compressing the base body portion 24, the second expansion portion 25, and the first expansion portion 23 of the packaging body 9. The base body portion 24, the second expansion portion 25, and the first expansion portion 23 of the packaging body 9 are not joined to each other, in each of the non-joining portion 37 and the non-joining portion 38.

As shown in FIG. 6, the other flap portion 7b is not overlapped with the joining portion 36a and the joining portion 36b in the width direction W. Further, the other flap portion 7b is overlapped with the non-joining portion 38 in the width direction W. In the same manner, one flap portion 7a is not overlapped with the joining portion 35a and the joining portion 35b in the width direction W. Further, one flap portion 7a is overlapped with the non-joining portion 37 in the width direction W. Accordingly, when taking off the absorbent article 3 from the packaging body 9 by grasping the longitudinal direction end portion 43 of the absorbent article 3 and the corresponding portion 45 of the longitudinal direction end portion 43 of the packaging body 9, it is difficult for the fixed portion 19 of the pair of flap portions 7 to be attached to the main body portion 5, etc., whereby the individual packaging body 1 has an excellent unsealing property.

As shown in FIG. 6, in one joining region 33 and the other joining region 34, the length:$L_1$ in the longitudinal direction L of the range in which the second expansion portion 25 and the non-joining portion 37 overlap with each other in the thickness direction (which is not shown) of the individual packaging body 1, is or longer than 50% of the length in the longitudinal direction L of the second expansion portion 25, that is, the distance:$D_1$ between the width direction second expansion line $WE_2$ and the width direction third expansion line $WE_3$. Accordingly, when the first expansion portion 23 is expanded, and the longitudinal direction end portion 43 of the absorbent article 3 and the corresponding portion 45 of the longitudinal direction end portion 43 of the packaging body 9 are grasped, it is easier for the pair of flap portions 7 and the second expansion portion 25 (especially, the end portion of the second expansion portion 25 on the opposite side of the base body portion 24) to be separated from each other, and for a space to be formed therebetween.

Further, as shown in FIG. 6, in one joining region 33, the length:$L_2$ in the longitudinal direction L of the joining portion 35b which extends from the width direction second expansion line $WE_2$, is or shorter than 40% of the distance: $D_2$ between the width direction first expansion line $WE_1$ and the width direction second expansion line $WE_2$. In the same manner, in the other joining region 34, the length:$L_2$ in the longitudinal direction L of the joining portion 36b which extends from the width direction second expansion line $WE_2$, is or shorter than 40% of the distance:$D_2$ between the width direction first expansion line $WE_1$ and the width direction second expansion line $WE_2$. Accordingly, when the first expansion portion 23 is expanded, and the longitudinal direction end portion 43 of the absorbent article 3 and the corresponding portion 45 of the longitudinal direction end portion 43 of the packaging body 9 are grasped, it is easier for the pair of flaps 7 and the second expansion portion 25 (especially, the end portion of the second expansion portion 25 on the opposite side of the base body portion 24) to be separated from each other, and for a space to be formed therebetween.

The individual packaging body 1 is, as shown in FIG. 5, folded in the width direction W, along a longitudinal direction first expansion line $LE_1$ and a longitudinal direction second expansion line $LE_2$ which are disposed on the inner side than the pair of joining regions 31 and extend along the longitudinal direction L. The longitudinal direction first expansion line $LE_1$ is disposed between the one side portion 15 in the longitudinal direction L of the packaging body 9 (the packaging sheet 11) and the longitudinal axis line LA of the packaging body 9 (the packaging sheet 11), and the longitudinal direction second expansion line $LE_2$ is disposed between the other side portion 16 in the longitudinal direction L of the packaging body 9 (the packaging sheet 11) and the longitudinal axis line LA of the packaging body 9 (the packaging sheet 11).

As shown in FIG. 5, the distance:$D_3$ between the longitudinal direction first expansion line $LE_1$ and the longitudinal direction second expansion line $LE_2$, is or shorter than ½ of a length:$L_3$ in the width direction W of the packaging body 9, and to be more specific, the length:$L_3$ between the one side portion 15 and the other side portion 16 in the longitudinal direction L of the packaging body 9 (the packaging sheet 11). Further, in a state in which the individual packaging body 1 is folded along the longitudinal direction first expansion line $LE_1$ and the longitudinal direction second expansion line $LE_2$ (the non-expansion state), as shown in FIG. 1, one region 39 of the packaging body 9 between the one side portion 15 and the longitudinal direction first expansion line $LE_1$ is disposed above the other region 40 of the packaging body 9 between the other side portion 16 and the longitudinal direction second expansion line $LE_2$. Accordingly, the other side portion 16 of the packaging body 9 is covered by the one region 39, whereby it is difficult for foreign matter, such as dust, etc., to enter therein from the other side portion 16.

In the individual packaging body 1, the one region 39 is fixed onto the other region 40 by the grasping portion 41.

The individual packaging body 1 is, as shown in FIG. 1, folded along the longitudinal direction first expansion line $LE_1$ and the longitudinal direction second expansion line $LE_2$, with the expansion end 27 of the first expansion portion 23 placed on the inner side. In other words, the expansion end 27 of the first expansion portion 23 is exposed by expanding the individual packaging body 1 which is in the non-expansion state, along the longitudinal direction first expansion line $LE_1$ and the longitudinal direction second expansion line $LE_2$. Accordingly, in a state in which the individual packaging body 1 is folded along the longitudinal direction first expansion line $LE_1$ and the longitudinal direction second expansion line $LE_2$ (the non-expansion state), it is difficult for foreign matter, such as dust, etc., to enter inside the individual packaging body 1 from the expansion end 27 of the first expansion portion 23.

Next, the unsealing method of the individual packaging body 1 according to the first embodiment is explained.

In the individual packaging body 1 in the non-expansion state as shown in FIG. 1, the grasping portion 41 is grasped, the one region 39 is expanded in the width direction W along the longitudinal direction first expansion line $LE_1$, and then the other region 40 is expanded in the width direction W along the longitudinal direction second expansion line $LE_2$, whereby the individual packaging body 1 in the half expansion state as shown in FIG. 5 is formed.

Incidentally, since the individual packaging body 1, in the non-expansion state, is folded along the longitudinal direction first expansion line $LE_1$ and the longitudinal direction second expansion line $LE_2$, with the expansion end 27 of the first expansion portion 23 placed on the inner side, it is difficult for the foreign matter, such as dust, etc., to enter inside the individual packaging body 1 from the expansion end 27 of the first expansion portion 23. Further, since the one region 39 of the packaging body 9 is disposed above the other region 40 of the packaging body 9, the other side portion 16 of the packaging body 9 is covered by the one region 39, whereby it is difficult for foreign matter, such as dust, etc., to enter therein from the other side portion 16.

Next, in the individual packaging body 1 in the half expansion state as shown in FIG. 5, the vicinity of the expansion end 27 of the first expansion portion 23 is grasped, and the first expansion portion 23 is expanded in the longitudinal direction L, along the width direction first expansion line $WE_1$, so as to put the individual packaging body 1 in the state as shown in FIG. 6.

Incidentally, in the individual packaging body 1 in the half expansion state as shown in FIG. 5, since one edge 27a in the width direction W of the expansion end 27 of the first expansion portion 23 is included in the joining portion 35b, and the other edge 27b in the width direction W thereof is included in the joining portion 36b, in the individual packaging body 1 in the non-expansion state, it is difficult for the expansion end 27 of the first expansion portion 23 to be unsealed by an unintended impact, etc., in a bag, etc.

Figure 7:
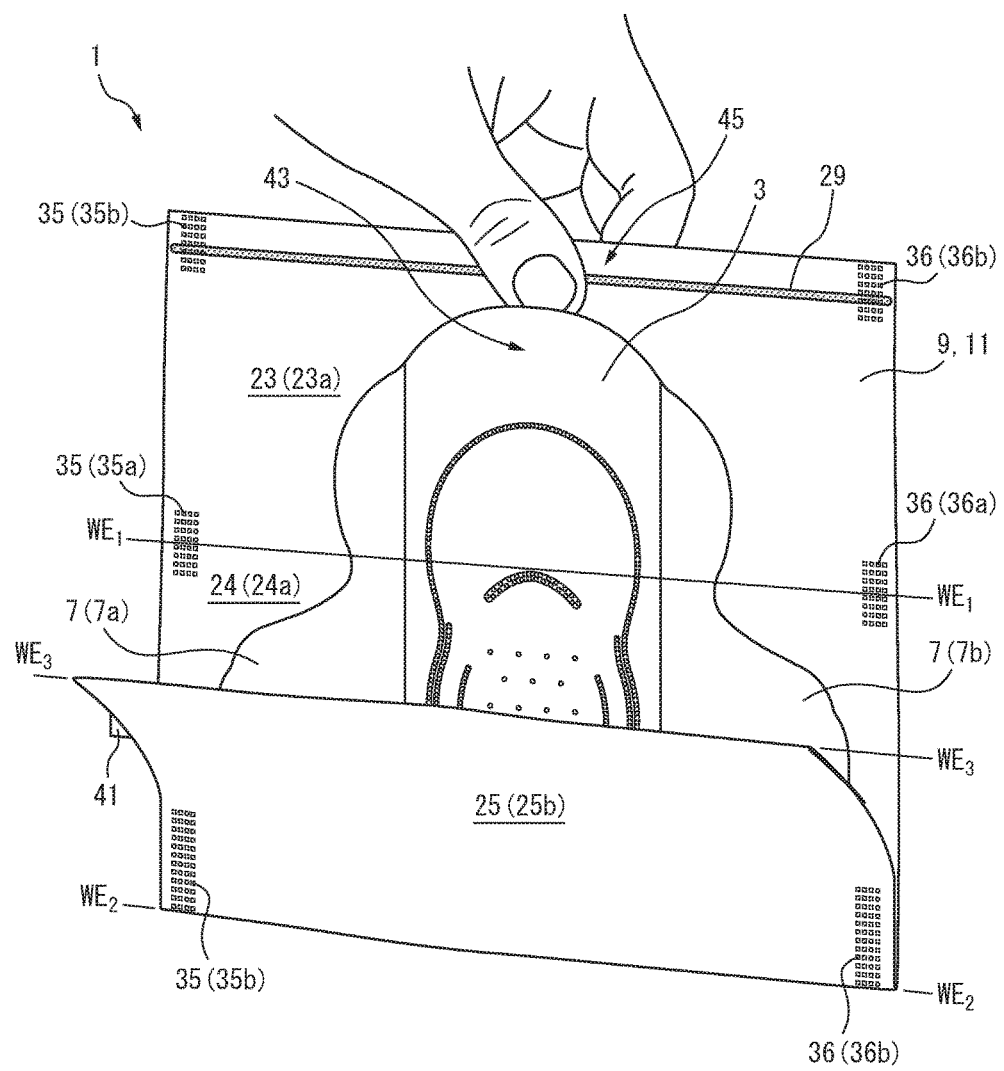
FIG. 7 is a view to explain the unsealing property of the individual packaging body 1 according to the first embodiment.
Figure 8:
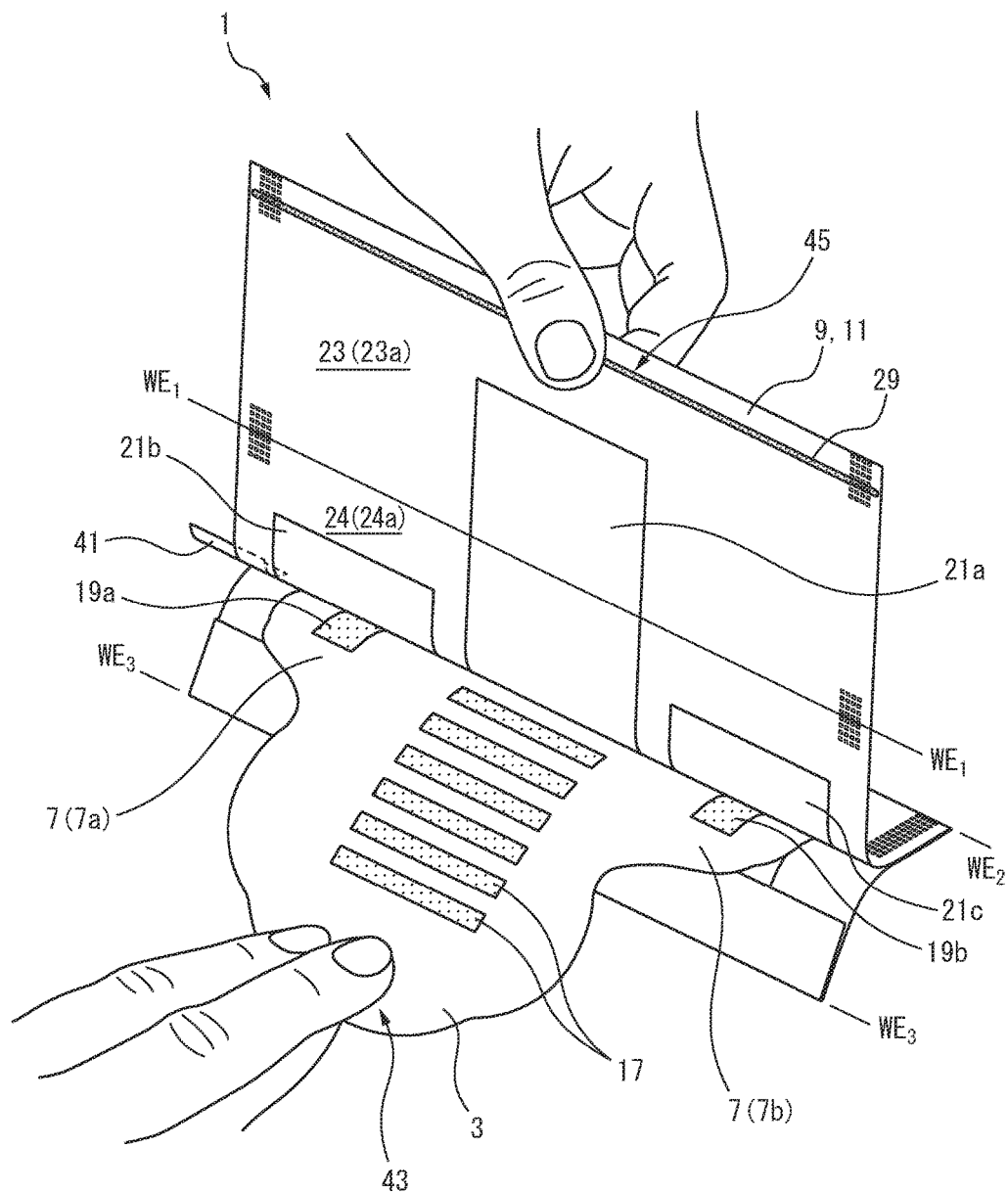
FIG. 8 is another view to explain the unsealing property of the individual packaging body 1 according to the first embodiment.

Next, in the individual packaging body 1 in the state as shown in FIG. 6, when the corresponding portion 45 of the packaging body 9 which corresponds to the longitudinal direction end portion 43 of the absorbent article 3 is grasped by a left hand, the individual packaging body 1 is to be in a state as shown in FIG. 7. To be more specific, a portion closer to the width direction third expansion line $WE_3$ of the second expansion portion 25 hangs downwards, the pair of flap portions 7 and the second expansion portion 25 are separated from each other, and a space is formed therebetween.

The followings may be mentioned as the reasons thereof.
(i) The second expansion portion 25 is disposed, in the longitudinal direction L, in a range which overlaps in the thickness direction of the individual packaging body 1 with the non-joining portion 37 and the joining portion 35b that extends from the width direction second expansion line $WE_2$.
(ii) The second expansion portion 25 is disposed, in the longitudinal direction L, in a range which overlaps in the thickness direction of the individual packaging body 1 with the non-joining portion 38 and the joining portion 36b that extends from the width direction second expansion line $WE_2$.
(iii) The length:$L_1$ in the longitudinal direction L of the range in which the second expansion portion 25 and the non-joining portion 37 overlap with each other in the thickness direction of the individual packaging body 1, is or longer than 50% of the length: $D_1$ in the longitudinal direction L of the second expansion portion 25.
(iv) The length:$L_1$ in the longitudinal direction L of the range in which the second expansion portion 25 and the non-joining portion 38 overlap with each other in the thickness direction of the individual packaging body 1, is or longer than 50% of the length: $D_1$ in the longitudinal direction L of the second expansion portion 25.
(v) In the one joining region 33, the length:$L_2$ in the longitudinal direction L of the joining portion 35b which extends from the width direction second expansion line $WE_2$, is or shorter than 40% of the distance:$D_2$ between the width direction first expansion line $WE_1$ and the width direction second expansion line $WE_2$.
(vi) In the other joining region 34, the length:$L_2$ in the longitudinal direction L of the joining portion 36b which extends from the width direction second expansion line $WE_2$, is or shorter than 40% of the distance:$D_2$ between the width direction first expansion line $WE_1$ and the width direction second expansion line $WE_2$.

Next, when the longitudinal direction end portion 43 of the absorbent article 3 is grasped by a right hand, and the absorbent article 3 is pulled forward so as to take off the absorbent article 3 from the packaging body 9, since the joining portions are not present on both ends in the width direction W of the packaging body until the fixed portion 19 of the pair of flap portions 7 is peeled off from the packaging body 9, and since it is difficult for the absorbent article 3 to come in contact with the second expansion portion 25, it is difficult for the fixed portion 19 of the pair of flap portions 7 to be suppressed from being peeled off from the packaging body 9. As a result, the absorbent article 3 is taken off from the packaging body 9 while not only the main body portion 5 of the absorbent article 3 but also the pair of flap portions 7 are curved toward the skin contact surface (the liquid permeable sheet 101) side thereof, whereby it is difficult for the fixed portion 19 of the pair of flap portions 7 to be attached to the main body portion 5, etc.

Figure 9:
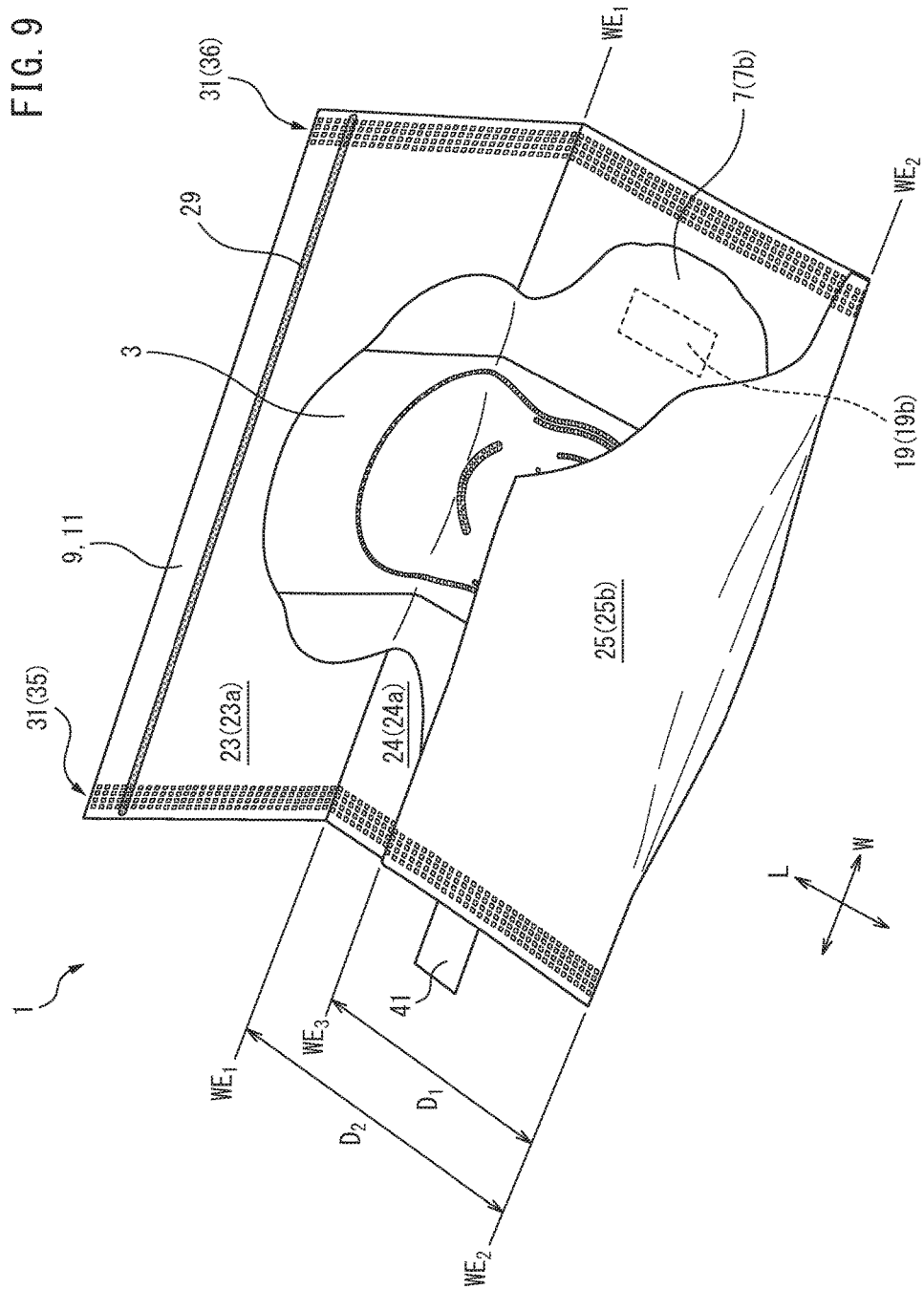
FIG. 9 is a view to explain the unsealing property of the individual packaging body 1 for comparison.
Figure 10:
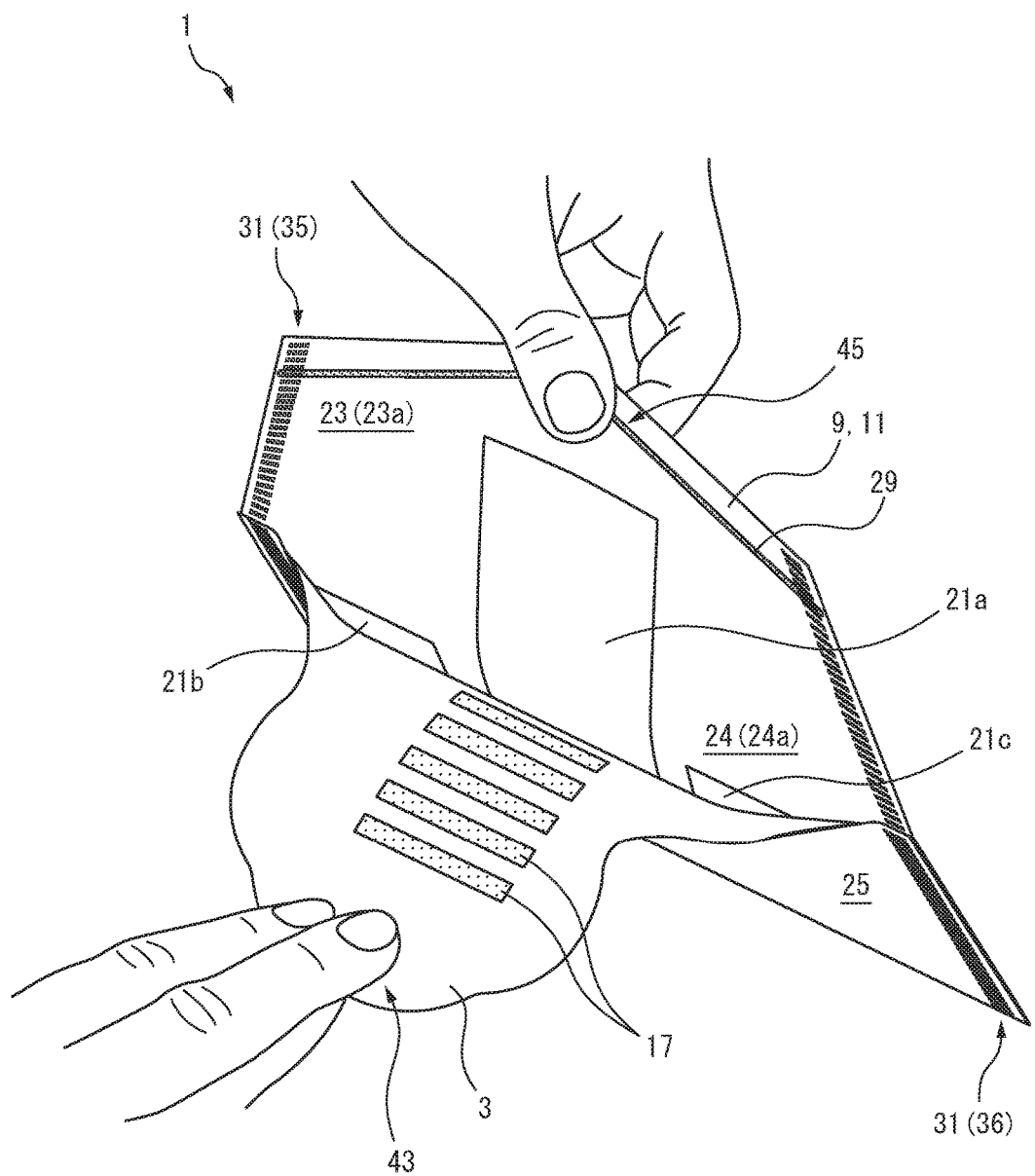
FIG. 10 is another view to explain the unsealing property of the individual packaging body 1 for comparison.

FIGS. 9 and 10 are views to explain the unsealing property of the individual packaging body 1 in which the packaging body 9 includes, on the outer side in the width direction W of the main body portion 5, the pair of joining regions 31 (which are one joining region 35 and the other joining region 36) which join the packaging body. The pair of joining regions 31 extend in the longitudinal direction L from the width direction first expansion line $WE_1$ to the width direction second expansion line $WE_2$ of the individual packaging body 1. Incidentally, FIGS. 9 and 10 correspond respectively to FIGS. 6 and 8.

The individual packaging body 1 as shown in FIGS. 9 and 10 is the same as the individual packaging body 1 as shown in the first embodiment, except for the following differences.
(i) The pair of joining regions 31 are respectively formed by the joining portion 35 and the joining portion 36, and the non-joining portion is not present.
(ii) In relation to (i), the second expansion portion 25 is disposed, in the longitudinal direction L, only in a range which overlaps in a thickness direction of the individual packaging body 1 with the joining portion 35 and the joining portion 36, that is, the both ends in the width direction W of the second expansion portion 25 are joined by the joining portion 35 and the joining portion 36, in the entirety in the longitudinal direction L.
(iii) The ratio of the distance:$D_1$ between the width direction second expansion line $WE_2$ and the width direction third expansion line $WE_3$ with respect to the distance:$D_2$ between the width direction first expansion line $WE_1$ and the width direction second expansion line $WE_2$ is higher than that in the first embodiment.
(That is, the width direction third expansion line $WE_3$ is close to the width direction first expansion line $WE_1$, and a large portion of the pair of flap portions 7 is hidden by the second expansion portion 25.)

The explanation for the configurations same as those in the individual packaging body 1 as shown in the first embodiment is omitted.

When the longitudinal direction end portion 43 of the absorbent article 3 is grasped by a right hand, the corresponding portion 45 of the packaging body 9 is grasped by a left hand, and the absorbent article 3 is pulled forward so as to take off the absorbent article 3 from the packaging body 9, since the both ends in the width direction W of the second expansion portion 25 are joined by the joining portion 35 and the joining portion 36, in the entirety in the longitudinal direction L, the fixed portion 19 of the pair of flap portions 7 is suppressed from being peeled off from the packaging body 9. Accordingly, in order to peel off the fixed portion 19 of the pair of flap portions 7 from the packaging body 9, it is required to pull the absorbent article 3 forward, to destroy the joining portion 35 and the joining portion 36, to separate the second expansion portion 25 from the base body portion 24, and to make the second expansion portion 25 and the base body portion 24 separated from each other. Accordingly, with the distance between the longitudinal direction end portion 43 of the absorbent article 3 and the fixed portion 19 of the pair of flap portions 7 being added, when the absorbent article 3 is pulled forward so as to take off the absorbent article 3 from the packaging body 9, the main body portion 5 of the absorbent article 3 is curved toward the skin contact surface (the liquid permeable sheet 101) side thereof, whereas the pair of flap portions 7 are curved toward the non-skin contact surface (the packaging body 9) side thereof, so as to be easily attached to the main body portion 5, etc., of the absorbent article 3.

In the individual packaging body 1 according to the first embodiment, the individual packaging body 1 is, expandable by the longitudinal direction first expansion line $LE_1$ and the longitudinal direction second expansion line $LE_2$, as well as expandable by the width direction first expansion line $WE_1$, the width direction second expansion line $WE_2$, and the width direction third expansion line $WE_3$, however, in the individual packaging body of the present disclosure, the packaging body has only to be expandable in at least one arbitrary direction. The above mentioned at least one arbitrary direction is preferably the longitudinal direction of the absorbent article. This is from the viewpoint of the effect of the present disclosure.

Figure 11:
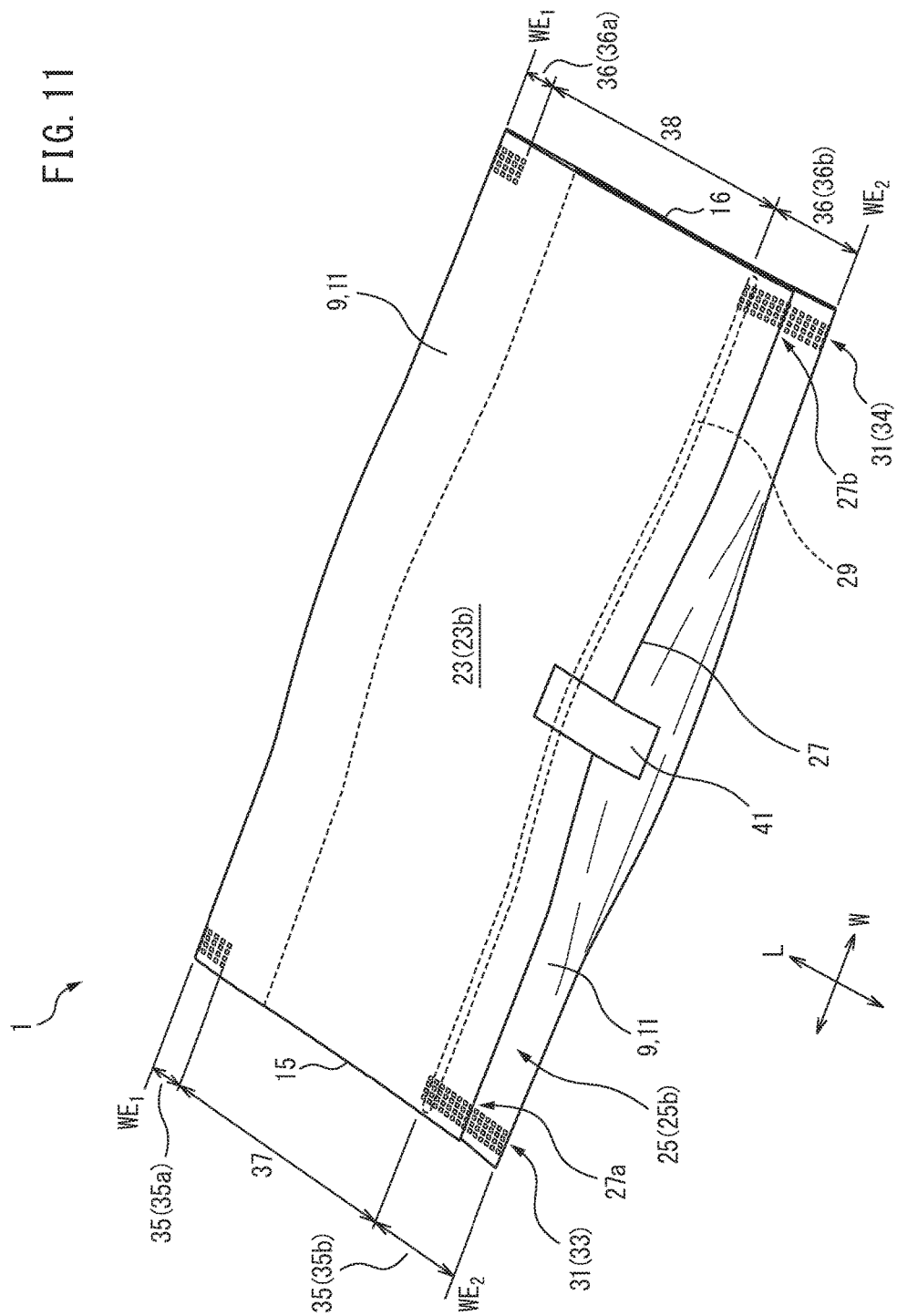
FIG. 11 is a perspective view of the individual packaging body 1 according to a second embodiment.

FIG. 11 is a perspective view of the individual packaging body 1 according to another embodiment (a second embodiment) of the present disclosure. The individual packaging body 1 according to the second embodiment is different from the individual packaging body 1 according to the first embodiment in that the individual packaging body is not folded by the longitudinal direction first expansion line $LE_1$ and the longitudinal direction second expansion line $LE_2$, and that the grasping portion 41 fixes the first expansion portion 23 and the second expansion portion 25. Since the portions other than such differences are the same as those in the individual packaging body 1 according to the first embodiment, the explanation thereof is omitted.

In the individual packaging body of the present disclosure, as the pair of flap portions, a pair of side flap portions, a pair of hip flap portions, etc., may be mentioned. In a case of an individual packaging body in which the absorbent article is taken off from the packaging body by grasping the longitudinal direction end portion on the front side of the absorbent article, the pair of flap portions are preferably a pair of side flap portions, and in a case of an individual packaging body in which the absorbent article is taken off from the packaging body by grasping the longitudinal direction end portion on the rear side of the absorbent article, the pair of flap portions are preferably a pair of hip flap portions.

Incidentally, the side flap portions are present in the center portion in the longitudinal direction of the absorbent article, and when the absorbent article is used, the side flap portions are generally folded toward the clothing contact surface side, so as to be fixed on the outer side of the clothing through a fixed portion, and the hip flap portions are present on the rear side in the longitudinal direction of the absorbent article, and when the absorbent article is used, the hip flap portions are generally not folded and are fixed on the inner side of the clothing through a fixed portion.

In the individual packaging body of the present disclosure, the main body portion and the pair of flap portions are fixed to the same surface of the packaging body through the fixed portion, however, in a case in which the individual packaging body does not include an expansion line, the above mentioned same surface means the entirety of one surface of the packaging sheet which configures the packaging body.

Further, in a case in which the packaging body includes an expansion line which extends in one direction, for example, a width direction expansion line which extends in the width direction of the absorbent article, the above mentioned same surface means the inner surface of the packaging body which is partitioned by the above mentioned width direction expansion line.

Still further, in a case in which the individual packaging body includes expansion lines which extend respectively in two or more directions, for example, a width direction expansion line which extends in the width direction of the absorbent article and a longitudinal direction expansion line which extends in the longitudinal direction of the absorbent article, the above mentioned same surface means the inner surface of the packaging body which is partitioned by the expansion line which extends in the direction orthogonal to the direction in which the absorbent article is taken out from the packaging body. For example, in a case in which the absorbent article is taken out from the packaging body in the longitudinal direction of the absorbent article, the above mentioned same surface means the inner surface of the packaging body which is partitioned by the width direction expansion line of the packaging body.

In the first embodiment, among the pair of joining regions 31, the joining portion 35 and the joining portion 36 are respectively formed by intermittently compressing the packaging body 9, however, in the individual packaging body of the present disclosure, the pair of joining regions may respectively be formed by a publicly known joining means in this technical field, for example, by an adhesive agent.

In the first embodiment, the one joining region 33 and the other joining region 34 respectively includes the joining portion 35a and the joining portion 36a which extend from the width direction first expansion line $WE_1$, the joining portion 35b and the joining portion 36b which extend from the width direction second expansion line $WE_2$, and the non-joining portion 37 and the non-joining portion 38 which are disposed therebetween, however, in the individual packaging body of the present disclosure, the joining portions and the non-joining portions may be disposed at an arbitrary portion, as long as the fixed portion of the pair of flap portions and the non-joining portion are overlapped with each other in the width direction of the absorbent article. For example, as a modification example of the first embodiment, a configuration in which the joining portions are disposed only in the vicinity of the width direction second expansion line, may be mentioned.

Incidentally, the individual packaging body of the present disclosure includes the above mentioned joining portions at an arbitrary position, whereby it is difficult for foreign matter, such as dust, etc., to enter inside the individual packaging body from the pair of joining regions.

Further, in a case in which the individual packaging body of the present disclosure includes a plurality of width direction expansion lines and a plurality of longitudinal direction expansion lines, and in which the packaging body includes, in the main body portion, the pair of joining regions which join the packaging body, on the outer side in the width direction of the absorbent article, the edges at the both side portions of the packaging body (which are the one side portion and the other side portion) in the longitudinal direction of the absorbent article, are aligned, whereby has an effect of being excellent in aesthetic appearance. This is because since an absorbent article generally has a certain thickness, when the individual packaging body is folded along the longitudinal direction expansion line, the above mentioned edges tend to be easily shifted.

In the individual packaging body of the present disclosure, the extending direction of the pair of joining regions of the packaging body is not particularly limited, as long as the pair of joining regions are present on the outer side of the absorbent article, however, the extending direction generally is the longitudinal direction of the absorbent article.

In the individual packaging body of the present disclosure, the non-joining portion may include one or a plurality of auxiliary joining portions, within the range which achieves the effect of the present disclosure. Accordingly, it is difficult for the position of the edges on both side portions of the packaging body in the longitudinal direction of the absorbent article to be shifted, whereby has an effect of being excellent in aesthetic appearance, etc. As the above mentioned auxiliary joining portions, an auxiliary compressed portion which is formed by compressing the packaging body (for example, a plurality of regions which are partitioned by an expansion line of the packaging body and are laminated with each other), an auxiliary adhesive portion which is formed by adhering the packaging body (for example, a plurality of regions which are partitioned by an expansion line of the packaging body and are laminated with each other) with an adhesive agent, etc., may be mentioned.

In the individual packaging body of the present disclosure, in a case in which the non-joining portion includes one or a plurality of auxiliary joining portions, from the viewpoint of securing the unsealing property of the individual packaging body, each of the above mentioned auxiliary joining portions preferably has a small area, and as the above mentioned auxiliary joining portions, for example, dotted auxiliary joining portions may be mentioned. Each of the above mentioned auxiliary joining portions has an area, preferably of 9 $mm^2$ or smaller, more preferably of 5 $mm^2$ or smaller, even more preferably of 3 $mm^2$ or smaller, and still even more preferably of 1 $mm^2$ or smaller. This is from the viewpoint of not suppressing the effect of the present disclosure.

In the individual packaging body of the present disclosure, in a case in which the non-joining portion includes one or a plurality of auxiliary joining portions, the area ratio of the auxiliary joining portions in the non-joining portion is preferably smaller than the area ratio of the actually joined portion in the joining portion (for example, the actually compressed portion, or the actually adhered portion). Further, the area ratio of the auxiliary joining portions in the non-joining portion is, preferably 50% or smaller, more preferably 30% or smaller, and even more preferably 10% or smaller of the area ratio of the actually joined portion in the joining portion. This is from the viewpoint of not suppressing the effect of the present disclosure. Incidentally, the above mentioned area and the area ratio mean the area ratio in the plane direction of the packaging body.

In the individual packaging body 1 according to the first embodiment, from the viewpoint of easily taking out the absorbent article 3, the second expansion portion 25 is disposed, in the longitudinal direction L, in a range which overlaps with the non-joining portion 37 and the joining portion 35b that extends from the width direction second expansion line $WE_2$ (with the non-joining portion 38 and the joining portion 36b that extends from the width direction second expansion line $WE_2$), in the thickness direction of the individual packaging body 1.

As a modification example of the first embodiment, a configuration in which a portion of the second expansion portion is disposed, in the longitudinal direction L, in a range which overlaps with the joining portion that extends from the width direction first expansion line, in the thickness direction of the individual packaging body, may be mentioned.

In the individual packaging body which satisfies the requirement of aspect 4, the length in the longitudinal direction of the absorbent article of the range in which the second expansion portion and the non-joining portion overlap with each other in the thickness direction of the individual packaging body 1, is or longer than, preferably 50% of, more preferably 60% of, and even more preferably 70% of, the length in the longitudinal direction of the absorbent article of the second expansion portion. This is from the view point of making the second expansion portion and the base body portion separated from each other, and forming a space therebetween, whereby to easily take out the absorbent article, when taking out the absorbent article from the packaging body.

In the individual packaging body which satisfies the requirement of aspect 4, the length in the longitudinal direction of the absorbent article of the joining portion disposed on the width direction second expansion line side, is or shorter than, preferably 40% of, more preferably of 30% of, and even more preferably of 25% of, the distance between the width direction first expansion line and the width direction second expansion line. This is from the view point of making the second expansion portion and the base body portion separated from each other, and forming a space therebetween, whereby to easily take out the absorbent article, when taking out the absorbent article from the packaging body.

In the individual packaging body 1 according to the first embodiment, the packaging body 9 includes three width direction expansion lines of the width direction first expansion line $WE_1$, the width direction second expansion line $WE_2$, and the width direction third expansion line $WE_3$, and two longitudinal direction expansion lines of the longitudinal direction first expansion line $LE_1$ and the longitudinal direction second expansion line $LE_2$, however, in the individual packaging body of the present disclosure, the packaging body may not include an expansion line. For example, the absorbent article is sandwiched by two packaging sheets, and the two packaging sheets or the folded one packaging sheet is joined so that the fixed portion of the pair of flap portions and the non-joining portion are overlapped with each other in the width direction of the absorbent article, whereby the individual packaging body of the present disclosure is formed.

Further, in the individual packaging body of the present disclosure, the absorbent article may not be expandable, that is, may not be folded.

Further, in a case in which the individual packaging body of the present disclosure includes a width direction expansion line which extends in the width direction of the absorbent article, the number of width direction expansion lines included in the individual packaging body is not particularly limited, and the individual packaging body may include, for example, two width direction expansion lines (a so-called three-fold, or a Z-shaped individual packaging body), three width direction expansion lines (a so-called four-fold, or a W-shaped individual packaging body), or four or more width direction expansion lines, etc.

Further, in a case in which the individual packaging body of the present disclosure includes a longitudinal direction expansion line which extends in the longitudinal direction of the absorbent article, the number of longitudinal direction expansion lines included in the individual packaging body is not particularly limited, and the individual packaging body may include, for example, one longitudinal direction expansion line which extends along the longitudinal axis of the absorbent article, or two longitudinal direction expansion lines, etc.

In the individual packaging body of the present disclosure, the individual packaging body preferably includes at least two width direction expansion lines which extend in the width direction of the absorbent article (the width direction first expansion line and the width direction second expansion line), and preferably further includes a first expansion portion which is partitioned by the width direction first expansion line, a base body portion which is partitioned by the width direction first expansion line and the width direction second expansion line, and a second expansion portion which is partitioned by the width direction second expansion line. Further, the pair of flap portions are preferably fixed to the above mentioned base body portion through a fixed portion. This is from the viewpoint of the effect of the present disclosure.

Further, the individual packaging body of the present disclosure may include three or more width direction expansion lines, as mentioned above, and in such cases, the second expansion portion is partitioned into a further plurality of expansion portions.

In the individual packaging body 1 according to the first embodiment, from the view point of making it difficult for the expansion end 27 of the first expansion portion 23 in the individual packaging body 1 to be unsealed by an unintended impact, etc., in a bag, etc., one edge 27a in the width direction W of the expansion end 27 of the first expansion portion 23 is included in the joining portion 35b, and the other edge 27b in the width direction W thereof is included in the joining portion 36b. However, in a case in which the individual packaging body of the present disclosure includes at least two width direction expansion lines which extend in the width direction of the absorbent article (the width direction first expansion line and the width direction second expansion line), and further includes a first expansion portion which is partitioned by the width direction first expansion line, a base body portion which is partitioned by the width direction first expansion line and the width direction second expansion line, and a second expansion portion which is partitioned by the width direction second expansion line, the one edge and/or the other edge in the width direction of the absorbent article, of the expansion end of the first expansion portion, may not be included in the joining portion.

In the individual packaging body 1 according to the first embodiment, from the viewpoint of making it difficult for foreign matter, such as dust, etc., to enter inside the individual packaging body 1, the distance:$D_3$ between the longitudinal direction first expansion line $LE_1$ and the longitudinal direction second expansion line $LE_2$, is or shorter than ½ of a length $L_3$ in the width direction W of the packaging body 9, and to be more specific, the length:$L_3$ between the one side portion 15 and the other side portion 16 in the longitudinal direction L of the packaging body 9 (the packaging sheet 11). Accordingly, the other side portion 16 of the packaging body 9 is covered by the one region 39, whereby it is difficult for foreign matter, such as dust, etc., to enter therein from the other side portion 16. However, in the individual packaging body which satisfies the requirements of aspect 7, the distance between the longitudinal direction first expansion line and the longitudinal direction second expansion line may be longer than ½ of the distance between the both side portions in the longitudinal direction of the absorbent article, of the packaging body.

In the individual packaging body 1 according to the first embodiment, the packaging sheet 11 includes the release papers 21a, 21b and 21c, respectively at portions which are in contact with the fixed portion 17 of the main body portion 5 of the absorbent article 3, the one flap portion 7a, and the other flap portion 7b, however, in the individual packaging body according to another embodiment of the present disclosure, a peeling process is performed on the inner surface to which the absorbent article of the packaging body (the packaging sheet) is fixed, whereby the above mentioned inner surface has a peeling property.

In the individual packaging body of the present disclosure, the packaging sheet which configures the packaging body is formed by a publicly known material in this technical field, and as the above mentioned material, for example, a fabric (for example, a nonwoven fabric, a woven fabric, and a knitted fabric), a film, a paper, and the laminate of these materials, etc., may be mentioned.

The absorbent article to be included in the individual packaging body of the present disclosure is not particularly limited, as long as the absorbent article includes the pair of flap portions, and for example, a sanitary napkin, a panty liner, etc., may be mentioned.

REFERENCE SIGNS LIST 1 individual packaging body
3 absorbent article
5 main body portion
7, 7a, 7b flap portion
9 packaging body
11 packaging sheet
13 one end portion
14 the other end portion
15 one side portion
16 the other side portion
17, 19, 19a, 19b fixed portion
21, 21a, 21b, 21c release paper
23 first expansion portion
24 base body portion
25 second expansion portion
27 expansion end
29 adhesive portion
31 joining region
33 one joining region
34 the other joining region
35, 36 joining portion
37, 38 non-joining portion
39 one region
40 the other region
41 grasping portion
43 longitudinal direction end portion
45 corresponding portion
LE1 longitudinal direction first expansion line
LE2 longitudinal direction second expansion line
WE1 width direction first expansion line
WE2 width direction second expansion line
WE3 width direction third expansion line

The invention claimed is:

1. An individual packaging body of an absorbent article, comprising the absorbent article which includes a longitudinal direction and a width direction, and a packaging body which envelops the absorbent article, wherein the absorbent article includes a main body portion which extends in the longitudinal direction, and a pair of flap portions which extend from the main body portion toward both side portions in the longitudinal direction, the main body portion and the pair of flap portions respectively have a fixed portion, and the main body portion and the pair of flap portions are fixed to a same surface of the packaging body through the respective fixed portions, the packaging body includes at least a width direction first expansion line and a width direction second expansion line each of which extending along the width direction for expanding the individual packaging body, the packaging body includes a first expansion portion, a base body portion, and a second expansion portion which are partitioned by the width direction first expansion line and the width direction second expansion line, and the same surface is an inner surface of the base body portion, the packaging body includes, on an outer side in the width direction of the main body portion, a pair of joining regions which join the packaging body and each of which including a joining portion and a non-joining portion, the fixed portion in each of the pair of flap portions and the non-joining portion are overlapped with each other in the width direction, and the individual packaging body is expandable in the width direction, along two longitudinal direction expansion lines which are disposed on an inner side than the pair of joining regions and extend in the longitudinal direction.

2. The individual packaging body according to claim 1, wherein each of the pair of joining regions includes the joining portion which is disposed on a width direction first expansion line side of the individual packaging body, the joining portion which is disposed on a width direction second expansion line side of the individual packaging body, and the non-joining portion which is disposed between the joining portions.

3. The individual packaging body according to claim 2, wherein the second expansion portion is disposed, in the longitudinal direction, in a range which overlaps with the non-joining portion and the joining portion that is disposed on the width direction second expansion line side in a thickness direction of the individual packaging body.

4. The individual packaging body according to claim 3, wherein a length in the longitudinal direction of the range in which the second expansion portion and the non-joining portion overlap with each other in the thickness direction of the individual packaging body, is or longer than 50% of a length in the longitudinal direction of the second expansion portion.

5. The individual packaging body according to claim 1, wherein at least one end portion in the width direction of an expansion end of the first expansion portion is included in the joining portion.

6. The individual packaging body according to claim 1, wherein a distance between the two longitudinal direction expansion lines is or shorter than ½ of a length in the width direction of the packaging body.

7. The individual packaging body according to claim 1, wherein an expansion end of the first expansion portion is exposed by expanding the individual packaging body along the two longitudinal direction expansion lines.

* * * * *